United States Patent
Bao et al.

(10) Patent No.: US 10,222,343 B2
(45) Date of Patent: Mar. 5, 2019

(54) METHOD AND APPARATUS FOR TESTING RESIDUAL STRESS IN COATINGS

(71) Applicant: China Building Material Test & Certification Group Co., Ltd., Beijing (CN)

(72) Inventors: Yiwang Bao, Beijing (CN); Delong Ma, Beijing (CN); Detian Wan, Beijing (CN); Xiaogen Liu, Beijing (CN)

(73) Assignee: China Build Material Test & Certification Group Co., Ltd., Beijing (CN)

( * ) Notice: Subject to any disclaimer, the term of this patent is extended or adjusted under 35 U.S.C. 154(b) by 81 days.

(21) Appl. No.: 15/351,387

(22) Filed: Nov. 14, 2016

(65) Prior Publication Data
US 2017/0241925 A1    Aug. 24, 2017

Related U.S. Application Data

(63) Continuation of application No. PCT/CN2016/074483, filed on Feb. 24, 2016.

(51) Int. Cl.
G01N 25/16 (2006.01)
G01L 5/00 (2006.01)

(52) U.S. Cl.
CPC .......... *G01N 25/16* (2013.01); *G01L 5/0047* (2013.01)

(58) Field of Classification Search
CPC ....... G01N 25/16; G01N 25/00; G01L 5/0047
See application file for complete search history.

(56) References Cited

PUBLICATIONS

Zhang et al., Residual Stress of Physical Vapor-Deposited Polycrystalline Multilayers, Feb. 2015, Science China, Physics, Mechanics & Astronomy, vol. 58, No. 2, 9 pp.*

(Continued)

*Primary Examiner* — Toan M Le
(74) *Attorney, Agent, or Firm* — Liu Law Office; Helen S. Liu

(57) ABSTRACT

Disclosed are a method and an apparatus for testing residual stress in coatings. The method includes: obtaining elastic modulus of a coating and a substrate of a target object; obtaining a temperature during the coating preparation of the target object; obtaining a cross-sectional area of the coating and a cross-sectional area of the substrate of the target object; obtaining a thermal expansion coefficient of the coating and a thermal expansion coefficient of the substrate of the target object; and calculating the coating residual stress $\sigma_c$ of the target object by the following formula:

$$\sigma_c = \left(\frac{S_s}{S_c}\right) \cdot \left[1 - \left(\frac{E_s S_s}{E_c S_c} + \frac{\alpha_c}{\alpha_s}\right) \bigg/ \left(1 + \frac{E_s S_s}{E_c S_c}\right)\right] \cdot E_s \alpha_s \Delta T_c,$$

wherein, $S_c$ is the cross-section area of the coating, $S_s$ is the cross-section area of the substrate, $E_c$ is the elastic modulus of the coating, $E_s$ is the elastic modulus of the substrate, $\alpha_c$ is the thermal expansion coefficient of the coating, $\alpha_s$ is the thermal expansion coefficient of the substrate, and $\Delta T_c$ is the temperature during the coating preparation.

12 Claims, 4 Drawing Sheets

(56) References Cited

PUBLICATIONS

Bao et al., Evaluating Elastic Modulus and Strength of Hard Coatings by Relative Method, 2007, Materials Science and Engineering A, vol. 458, pp. 268-274.*

Bao et al., Evaluating Mechanical Properties of Hard Coatings by Using Relativity Method, Online Jul. 15, 2006, Key Engineering Materials, vol. 313, pp. 53-58.*

* cited by examiner

METHOD AND APPARATUS FOR TESTING RESIDUAL STRESS IN COATINGS

CROSS REFERENCE TO RELATED APPLICATIONS

This application is a continuation of International Application No. PCT/CN2016/074483, filed on Feb. 24, 2016, the entire contents of which are incorporated herein by reference.

TECHNICAL FIELD

The present disclosure relates to the technical field of residual stress testing for coatings, and more particularly, to a method and an apparatus for testing residual stress in coatings.

BACKGROUND

For improving the strength, hardness, high temperature resistance, corrosion resistance and wear resistance of the component, the existing technology often plating coatings on metal or other solid materials by chemical or physical method. The coating component has important significance in improving the performance of modern machinery, including automotive, aerospace, and various high temperature wear resistance devices. Evaluation of the mechanical properties of coating must be solved in the engineering application, so as to improve the process and its service life. Residual stress, which is one of the vital parameters of coating, is the stresses existing in the target object and maintaining self-balance, at the condition of zero applied loadings. Both coating and substrate are prepared at high temperature and then cooled to room temperature generally. During this process, due to the mismatch of thermal expansion coefficient between coating and substrate, the smaller thermal expansion coefficient side is under tensile stress, while the larger thermal expansion coefficient side is under compressive stress. This is the main reason for residual stress generated in coating. The existing of residual tensile stress may cause micro cracks in the coating, which reduce the structure performance and have a great influence on its resistance of oxidation, corrosion and high temperature. Therefore, accurately determining the residual stress in coatings has great significance.

At present, the commonly used methods for testing residual stress in coatings mainly include the curvature measurement method based on Stoney formula or the X-ray diffraction method.

For curvature measurement method based on Stoney formula, the principle is that the single-face coated substrate will generate bending deformation under the effect of residual stress. In many cases, the curvature radius can be measured by laser interference instrument or surface contour graph. The residual stress of coating can be calculated by using the Stoney formula according to substrate curvature radius. However, there are some problems in this method: due to the curvature of coated sample is small and it does not equal along the length direction, the curvature is difficult to be measured accurately. In addition, most components are symmetrical coated or in asymmetrical state for which the stiffness of the substrate is much larger than that of the coating, thus no bending deformation could be measured. In fact, Stoney formula is available only for single-face coating and thin substrate sample. Since the residual stress is not a material constant, the measured residual stress in the coating by Stoney formula reflects the stress in the testing piece, not real stress in symmetrical components.

For X-ray diffraction method, its principle is using X-ray diffraction to measure the elastic strain results from the lattice spacing change which is caused by stress. Test samples are often using powder or small blocks, so it only reflects partial performance of sample and it cannot represent the residual stress of the whole component. Meanwhile, the results of the X-ray diffraction method are inaccurate and have large divergence.

It must be emphasized that the residual stress is not a material constant. For the same kind of coating, when the sizes of substrates are different, the residual stress in coating is also different. For the actual service coating, the above mentioned methods are difficult to be used in site.

SUMMARY

In this situation, the present disclosure provides a method and an apparatus for testing residual stress in coatings simply and accurately.

In order to achieve the purpose, the present disclosure mainly provides the following technical proposal.

On one side, the embodiments of the present disclosure provide a method for testing residual stress in coatings, including the following steps:

obtaining elastic modulus of a coating and a substrate of a target object;

obtaining a temperature during the coating preparation of the target object;

obtaining a cross-sectional area of the coating and a cross-sectional area of the substrate of the target object;

obtaining a thermal expansion coefficient of the coating and a thermal expansion coefficient of the substrate of the target object; and calculating the coating residual stress $\sigma_c$ of the target object by the following formula:

$$\sigma_c = \left(\frac{S_s}{S_c}\right) \cdot \left[1 - \left(\frac{E_s S_s}{E_c S_c} + \frac{\alpha_c}{\alpha_s}\right) \middle/ \left(1 + \frac{E_s S_s}{E_c S_c}\right)\right] \cdot E_s \alpha_s \Delta T_c,$$

wherein, $S_c$ is the cross-section area of the coating of the target object, $S_s$ is the cross-section area of the substrate of the target object, $E_c$ is the elastic modulus of the coating of the target object, $E_s$ is the elastic modulus of the substrate of the target object, $\alpha_c$ is the thermal expansion coefficient of the coating of the target object, $\alpha_s$ is the thermal expansion coefficient of the substrate of the target object, and $\Delta T_c$ is the temperature during the coating preparation of the target object.

Preferably, an average thermal expansion coefficient of the coating of the target object from room temperature to the preparation temperature $\Delta T_c$ of the coating is determined as the thermal expansion coefficient $\alpha_c$ of the coating, and an average thermal expansion coefficient of the substrate of the target object from room temperature to the preparation temperature $\Delta T_c$ of the coating is determined as the thermal expansion coefficient $\alpha_s$ of the substrate, when the thermal expansion coefficient $\alpha_c$ of the coating and the thermal expansion coefficient $\alpha_s$ of the substrate of the target object are tested.

Preferably, the average thermal expansion coefficient of the coating and the average thermal expansion coefficient of the substrate of the target object are obtained by using a relative method.

Preferably, the thermal expansion coefficient $\alpha_c$ of the coating and the thermal expansion coefficient $\alpha_s$ of the substrate of the target object are obtained through the following steps:

preparing a sample A and a sample B, wherein the sample A is a sample of the substrate of the target object, and the sample B is a compound sample of which the substrate of the target object is compounded with the coating of the target object;

obtaining the thermal expansion coefficients of the sample A and the sample B separately, wherein the thermal expansion coefficient of the sample A is the thermal expansion coefficient $\alpha_s$ of the substrate of the target object; and obtaining the thermal expansion coefficient $\alpha_c$ of the coating of the target object through the thermal expansion coefficients of the sample A and the sample B.

Preferably, the substrates of the sample A and the sample B are prepared from the same material as the substrate of the target object, and the coating of the sample B is prepared from the same material and preparation process as the coating of the target object.

Preferably, the distribution of the coating of the sample B is symmetrical on the substrate of the sample B, so as to avoid bending deformation during temperature changing.

Preferably, sizes of both the sample A and the sample B adopt a sample size according to a test standard of thermal expansion coefficient.

Preferably, the elastic modulus of the coating and the substrate of the target object are obtained by using a relative method.

Preferably, the elastic modulus of the coating and the substrate of the target object are obtained by testing samples prepared from the same material as the target object.

Preferably, coating residual stress type of the target object is determined according to the thermal expansion coefficient of the coating and the thermal expansion coefficient of the substrate of the target object, wherein if the thermal expansion coefficient of the coating is larger than the thermal expansion coefficient of the substrate, the coating residual stress is tensile stress, and otherwise, the coating residual stress is compressive stress.

On the other hand, the embodiments of the present disclosure provide an apparatus for testing residual stress in coatings, including:

a heating furnace, for heating a sample in order to make the sample expand with heat;

a temperature control device, for controlling heating temperature of the heating furnace;

a slide rail mechanism, for being connected with the heating furnace, the heating furnace sliding along a track of the slide rail mechanism;

a quartz bracket, provided with a sample holder;

a drive rod, for transferring expansion displacement of the sample;

a micro displacement measurement device, for testing the expansion displacement of the sample transferred by the drive rod; and a computer, for receiving relevant data and organizing the relevant data into parameters for calculating the coating residual stress, and obtaining the coating residual stress $\sigma_c$ of the target object through processing the parameters according to the following formula:

$$\sigma_c = \left(\frac{S_s}{S_c}\right) \cdot \left\{1 - \left[\frac{E_s S_s}{E_c S_c} + \frac{\alpha_c}{\alpha_s}\right] \Big/ \left[1 + \frac{E_s S_s}{E_c S_c}\right]\right\} \cdot E_s \cdot \alpha_s \cdot \Delta T_c,$$

wherein, $S_c$ is the cross-section area of the coating of the target object, $S_s$ is the cross-section area of the substrate of the target object, $E_c$ is the elastic modulus of the coating of the target object, $E_s$ is the elastic modulus of the substrate of the target object, $\alpha_c$ is the thermal expansion coefficient of the coating of the target object, $\alpha_s$ is the thermal expansion coefficient of the substrate of the target object, and $\Delta T_c$ is the temperature during the coating preparation of the target object.

Preferably, the quartz bracket comprises a first quartz bracket and a second quartz bracket, which are internally provided with the sample holder separately for holding a sample; and the drive rod comprises a first drive rod and a second drive rod, which are used for transferring the expansion displacement of the samples in the first quartz bracket and the second quartz bracket separately.

Preferably, test resolution of the micro displacement measurement device is smaller than 0.2 mm.

Compared with the prior art, the present disclosure has the following beneficial effects:

The method provided by the embodiments of the present disclosure can be used to evaluate the residual stress of any isothermal coating component, of which the coating and the substrate are under same temperature during preparation and cooling process. The method provided by the embodiments of the present disclosure is simple and has nice operability without the limits in the shape of coated component, and it is convenient to obtain the coating residual stress by simple sample preparation. The test results of the method provided by the embodiments of the present disclosure are accurate and low in dispersion. Not only can the value of the residual stress be obtained, the type of the coating residual stress (tensile stress or compressive stress) can also be determined.

BRIEF DESCRIPTION OF THE DRAWINGS

FIG. 6-1 shows a front view of the force schematic diagram of the graphite substrate/CVD silicon carbide coating pipes in accordance with an embodiment of the present disclosure.

FIG. 6-2 shows a side view of the force schematic diagram of the graphite substrate/CVD silicon carbide coating pipes in accordance with an embodiment of the present disclosure.

FIG. 6-3 shows a top view of the force schematic diagram of the graphite substrate/CVD silicon carbide coating pipes in accordance with an embodiment of the present disclosure.

FIG. 9-1 shows a front view of the force schematic diagram of the graphite substrate/CVD silicon carbide coating plates in accordance with an embodiment of the present disclosure.

FIG. 9-2 shows a side view of the force schematic diagram of the graphite substrate/CVD silicon carbide coating plates in accordance with an embodiment of the present disclosure.

FIG. 9-3 shows a top view of the force schematic diagram of the graphite substrate/CVD silicon carbide coating plates in accordance with an embodiment of the present disclosure.

DETAILED DESCRIPTION

Further detailed description will be given below combine with the embodiments of the present disclosure, but not as the restrictions. In the following descriptions, different "one embodiment" or "embodiment" may not refer to the same embodiment. In addition, the specific features, structure or features in one or more embodiment can be combined by any suitable form.

Figure 1:
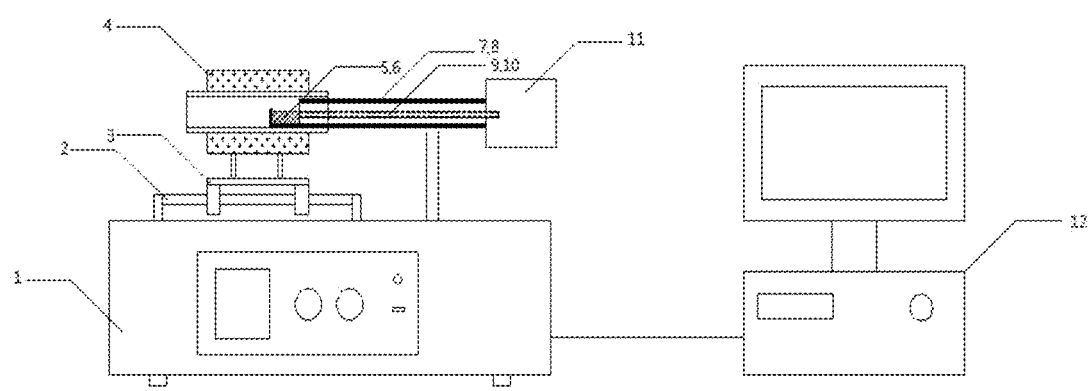
FIG. 1 shows a structural diagram of an apparatus for testing residual stress in coatings in accordance with an embodiment of the present disclosure.
Figure 2:
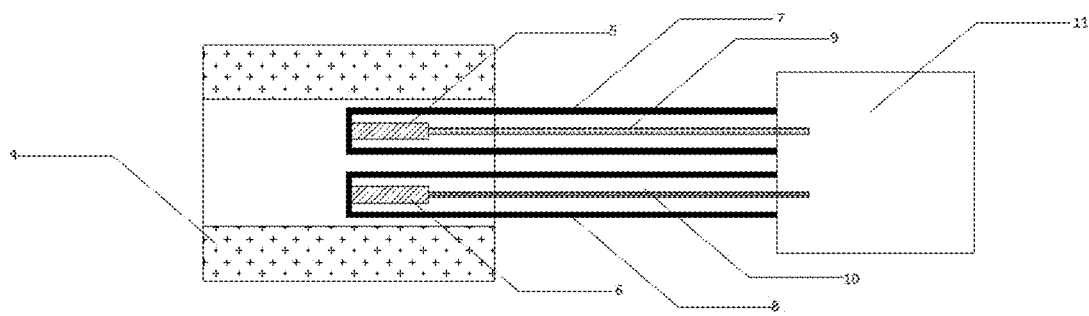
FIG. 2 shows a structural diagram of an expansion coefficient measuring part in accordance with an embodiment of the present disclosure.

FIG. 1 shows the structural diagram of the apparatus for testing residual stress in coatings of the present disclosure in the embodiment. FIG. 2 shows the structural diagram of expansion coefficient measuring part. As shown in FIG. 1 and FIG. 2, the apparatus for testing residual stress in coatings includes the following parts:

a heating furnace 4, for heating a sample in order to make the sample expand with heat;

a temperature control device 1, for controlling the heating temperature of the heating furnace 4;

a slide rail mechanism, for being connected with the heating furnace 4, the heating furnace 4 sliding along the track 2 of the slide rail mechanism;

a quartz bracket, provided with a sample holder;

a drive rod, for transferring the expansion displacement of the sample;

a micro-displacement measurement device 11, for testing the sample expansion displacement transferred by the drive rod;

a computer 12, for receiving the relevant data and organizing the relevant data into parameters for the calculation of the coating residual stress, and obtaining the coating residual stress $\sigma_c$ of the target object through processing the parameters according to the following formula:

$$\sigma_c = \left(\frac{S_s}{S_c}\right) \cdot \left\{1 - \left[\frac{E_s S_s}{E_c S_c} + \frac{\alpha_c}{\alpha_s}\right] \middle/ \left[1 + \frac{E_s S_s}{E_c S_c}\right]\right\} \cdot E_s \cdot \alpha_s \cdot \Delta T_c,$$

where, $S_c$ is the cross-section area of the coating of the target object, $S_s$ is the cross-section area of the substrate of the target object, $E_c$ is the elastic modulus of the coating of the target object, $E_s$ is the elastic modulus of the substrate of the target object, $\alpha_c$ is the thermal expansion coefficient of the coating of the target object, $\alpha_s$ is the thermal expansion coefficient of the substrate of the target object, and $\Delta T_c$ is the temperature during the coating preparation of the target object.

The original data processed by the computer 12 of the present disclosure in the embodiment can be either manually input by input devices or the measured data can be transmitted to the computer directly through the measuring mechanism by a wired or wireless way. Such as the expansion displacement data measured by the micro displacement measuring device 11, that data can be transmitted to the computer directly, also can be manually input after manually read. The needed residual stress value that the computer 12 received after automatic processing of the present disclosure in the embodiment can judge whether the residual stress is compressive or tensile stress at the same time.

FIG. 2 shows the structural diagram of the expansion coefficient measuring part of the present disclosure in the embodiment as shown in FIG. 1 and FIG. 2. As a preferred embodiment, the quartz bracket including a first quartz bracket 7 and a second quartz bracket 8, the first quartz bracket 7 and the second quartz bracket 8 are internally provided with the sample holder separately to hold a sample (the first sample holder 5 is in the first quartz bracket 7, and the second sample holder 6 is in the second quartz bracket 8) separately.

The drive rod includes a first drive rod 9 and a second drive rod 10, the first drive rod 9 and the second drive rod 10 are used for transferring the expansion displacement of the samples in the first quartz bracket 7 and the second quartz bracket 8, respectively. In the embodiment, thermal expansion coefficients of two samples can be measured simultaneously to ensure the data accuracy and simplify the operation.

As a preferred embodiment, the test resolution of the micro displacement measurement device 11 is smaller than 0.2 mm. The micro displacement measuring device 11 can adopt an inductive micro displacement measuring device, a differential transformer type micro displacement measuring device, a micro eddy current displacement measuring device or a Hall sensor. The measured data can be transmitted to the computer 12 for processing directly in order to obtain the required parameters.

The apparatus in the embodiment of the present disclosure also includes other devices to measure the needed data, such as an elastic modulus measuring device which is used to obtain the needed data for obtaining a corresponding elastic modulus. Also, as mentioned above, the data measured by the elastic modulus measuring device can be transmitted to the computer 12 directly or manually input to the computer 12 after read manually. In addition, the apparatus in the embodiment of the present disclosure also includes the devices for measuring the size data.

The specific structure of the slide rail mechanism in the embodiment of the present disclosure is not restricted, as long as the heating furnace 4 can be moved smoothly to achieve sample measurement. In the embodiment, the slide rail mechanism includes a track 2 and a sliding bearing 3 that can slide along the track 2. The heating furnace 4 and the sliding bearing 3 are fixed, thus the heating furnace 4 can do reciprocation motion with the sliding bearing 3 together along the track 2.

Figure 3:
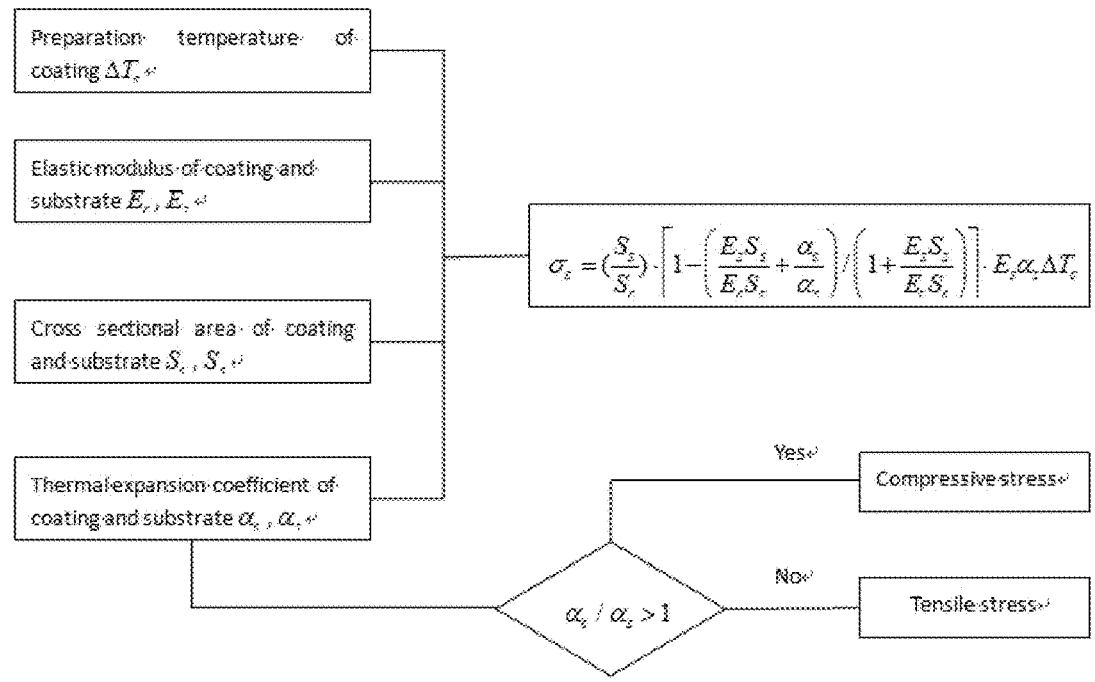
FIG. 3 shows a flaw chart of a method for testing residual stress in coatings in accordance with an embodiment of the present disclosure.

FIG. 3 shows the flaw chart of the method for testing residual stress in coatings in an embodiment of the present disclosure. As shown in FIG. 3, the method for testing residual stress in coatings includes the following steps:

obtaining an elastic modulus of a coating and a substrate of a target object;

obtaining a temperature during the coating preparation of the target object;

obtaining a cross-sectional area of the coating and a cross-sectional area of the substrate of the target object;

obtaining a thermal expansion coefficient of the coating and a thermal expansion coefficient of the substrate of the target object; and calculating the coating residual stress $\sigma_c$ of the target object by the following formula:

$$\sigma_c = \left(\frac{S_s}{S_c}\right) \cdot \left\{1 - \left[\frac{E_s S_s}{E_c S_c} + \frac{\alpha_c}{\alpha_s}\right] \middle/ \left[1 + \frac{E_s S_s}{E_c S_c}\right]\right\} \cdot E_s \cdot \alpha_s \cdot \Delta T_c,$$

where, $S_c$ is the cross-section area of the coating of the target object, $S_s$ is the cross-section area of the substrate of the target object, $E_c$ is the elastic modulus of the coating of the target object, $E_s$ is the elastic modulus of the substrate of the target object, $\alpha_c$ is the thermal expansion coefficient of the coating of the target object, $\alpha_s$ is the thermal expansion coefficient of the substrate of the target object, and $\Delta T_c$ is the temperature during the coating preparation of the target object.

The method in the embodiment of the present disclosure can be used to evaluate the coating residual stress of any isothermal coating component, of which the coating and the substrate are under same temperature during preparation. The method provided by the embodiment of the present disclosure is simple and high in operability without the restrictions of the shape of coating component, while it is convenient to obtain the coating residual stress by simple sample preparation. The test result of the method in the embodiment of the present disclosure is accurate and low in dispersion. Not only can the value of the residual stress be obtained, the type of the coating residual stress (tensile stress or compressive stress) can also be determined. The required data in the present disclosure can be obtained by using the test apparatus above.

As a preferred embodiment, the thermal expansion coefficient $\alpha_c$ of the coating and the thermal expansion coefficient $\alpha_s$ of the substrate are the average heat expansion coefficient (from the room temperature to the preparation temperature of coating $\Delta T_c$) of the coating and the substrate. The average thermal expansion coefficient of the coating and the substrate of the target object can be measured in any item in the prior art.

As a preferred embodiment, the thermal expansion coefficient $\alpha_c$ of the coating of the target object and the thermal expansion coefficient $\alpha_s$ of the substrate can be obtained by the following steps:

preparing sample A and sample B, wherein sample A is a sample of the substrate of the target object, and sample B is a compound sample of which the substrate of the target object is compounded with the coating of the target object;

obtaining the thermal expansion coefficients of sample A and sample B separately, wherein the thermal expansion coefficient of sample A is the thermal expansion coefficient $\alpha_s$ of the substrate of the target object;

obtaining the thermal expansion coefficient $\alpha_c$ of the coating of the target object through the thermal expansion coefficients of sample A and sample B.

Relevant data are obtained through the samples which are prepared and measured easily, and therefore it is not restricted by the actual target object. The quantitative (size) and qualitative (type) evaluation of the coating residual stress are achievable in any coating component.

The substrates of sample A and sample B are prepared from the same material as the substrate of the target object, and the coating of the sample B is prepared from the same material and preparation process as the coating of the target object. Since the materials are the same, the expansion coefficient of the sample is the relevant expansion coefficient of the target object.

As a preferred embodiment, the distribution of the coating of sample B is symmetrical on the substrate of sample B, to avoid the bending deformation by temperature changing.

The sizes of both sample A and sample B adopt the sample size according to the test standard coefficient of thermal expansion, so as to facilitate the measurement of the thermal expansion coefficient. If both sample A and sample B are cuboid, the minimum length of sample A and sample B is 50 mm, any side of the cross section is less than 6 mm, and the cross-sectional area is more than 10 mm². When this shape is adopted, the coating is at least deposited on the two opposites of the sample so as to form a symmetrical to avoid bending deformation by temperature changing.

As a preferred embodiment, the elastic modulus of the coating and the substrate of the target object are obtained through the relative method. Of course, it also can be obtained by any other appropriate methods.

As a preferred embodiment, the elastic modulus of the coating and the substrate of the target object are obtained by testing the samples prepared from the same material as the target object. The samples can refer to the sample A and sample B described above.

As a preferred embodiment, the coating residual stress types of the target object are determined according to the thermal expansion coefficient of the coating and the substrate of the target object. If the thermal expansion coefficient of coating of the target object is larger than the thermal expansion coefficient of the substrate, the residual stress of the coating is tensile stress. Otherwise, the residual stress of coating is compressive stress. The embodiment of the present disclosure can not only determine the value of residual stress, but also can determine the type of residual stress.

Take the actual residual stress test of coating components as an example to further illustrate the method and apparatus of the present disclosure.

Embodiment 1: the residual stress test of graphite substrate/CVD silicon carbide coating circular pipes.

Figure 4:
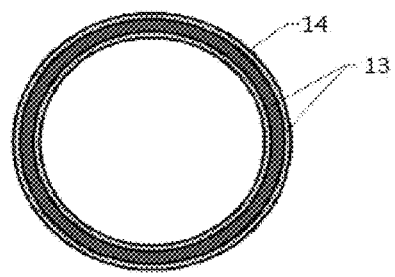
FIG. 4 shows a schematic diagram of the cross section of the graphite substrate/CVD (chemical vapor deposition) silicon carbide coating pipes in accordance with an embodiment of the present disclosure.

The graphite substrate/CVD silicon carbide coating circular pipes are provided, the schematic diagram of the cross section thereof is as shown in FIG. 4, the label 13 in FIG. 4 is silicon carbide coating, and label 14 is graphite substrate; the outer radius of the pipe R1 is 330 mm, the inner radius R2 is 320 mm, the length L is 400 mm, the outer coating thickness T1 is 200 μm, and the inner coating thickness T2 is 200 μm.

Figure 5:
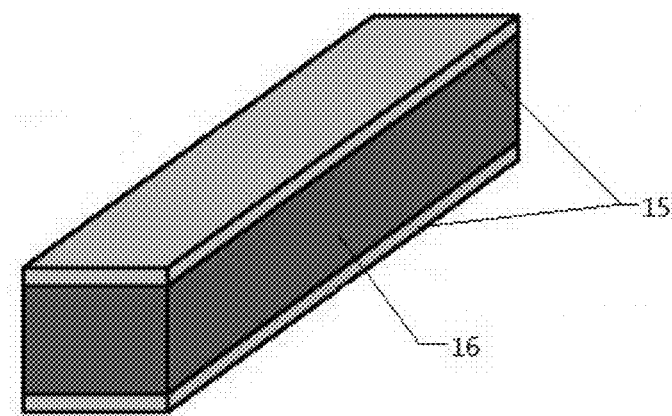
FIG. 5 shows a schematic diagram of the sample B in accordance with an embodiment of the present disclosure.

Both sample A and sample B are long bar with length of 50 mm, the length of the cross section thereof is 4 mm and the width is 3 mm, and the cross-sectional area is 12 mm². The schematic diagram of taken sample B is as shown in FIG. 5, the label 15 in FIG. 5 is silicon carbide coating, and label 16 is graphite substrate. And the upper and lower coating thicknesses are both 200 μm; the same material is adopted for sample A and the graphite substrate of to be measured pipes, the sample B and to be measured graphite substrate/CVD silicon carbide coating pipes uses the same preparation process, and the preparation temperature $\Delta T_c$ of the coating is 1000° C.

The elastic modulus of the CVD silicon carbide coating and the graphite substrate are obtained by testing sample A and sample B using the relative method (specific operation refers to international standard "Test method for determining elastic modulus and strength of thick ceramic coatings" (ISO/TC 206 AWI 19603)). Specifically, the elastic modulus Ec of the silicon carbide coating is 440 GPa, and the elastic modulus Es of the graphite substrate is 9.8 GPa.

Figures 1, 2, 6:
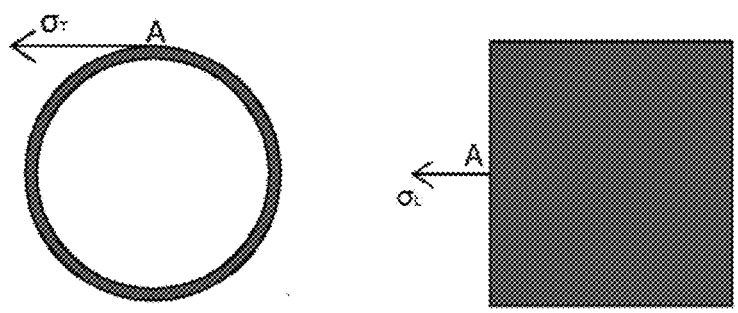
Figures 3, 6:
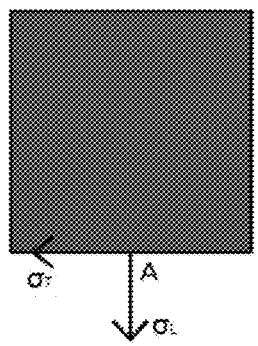

The residual stress of the to be measured graphite substrate/CVD silicon carbide coating pipes is divided into tangential residual stress $\sigma_T$ and axial direction (along round tube length direction) residual stress $\sigma_L$, and the front view, side view and top view of the force schematic view are shown in FIGS. 6-1 to 6-3, respectively.

The measurement of the tangential residual stress $\sigma_T$ of to be measured graphite substrate/CVD silicon carbide coating pipes is as follows:

In order to test the residual stress in the tangential direction of the round pipe coating, and the cross-sectional area ratio of the pipe should be determined. The area of the coating is $S_c=\pi((R_1+T_1)^2-R_1^2+R_2^2-(R_2-T_2)^2)=8.16\times10^2$ mm$^2$, and the cross-sectional area of the substrate is $S_s=\pi(R_1^2-R_2^2)=2.04\times10^4$ mm$^2$. Sample A and sample B are tested by the apparatus for testing residual stress in coatings and the average thermal expansion coefficients of the coating and the substrate of the samples are obtained. In particular, the thermal expansion coefficient $\alpha_c$ of the coating is $2.47\times10^{-6}/°$ C., the thermal expansion coefficient $\alpha_s$ of the substrate is $1.63\times10^{-6}/°$ C. The elastic modulus of the coating and the substrate of the samples, the cross-sectional areas of the coating and the substrate and the preparation temperature of the coating are input into the computer 12, and the residual stress of the coating of the component can be output. Specifically, the tangential residual stress $\sigma_T$ of the graphite substrate/CVD silicon carbide coating pipes should be 132.19 MPa. Since the thermal expansion coefficient of the coating is greater than that of the substrate, the type of obtained residual stress of the coating is tensile stress.

The axial direction residual stress $\sigma_L$ of to be measured graphite substrate/CVD silicon carbide coating pipes is as follows:

The cross-sectional area of the coating is $S''_c=L\times(T_1+T_2)=160$ mm$^2$, the cross-sectional area of the substrate is $S'_s=L\times(R_1-R_2)=4\times10^3$ mm$^2$. The elastic modulus of the coating and the substrate, the cross-sectional area of the coating and the substrate and the preparation temperature of the coating are input into the test apparatus, and the coating residual stress of the measured component can be obtained. The axial direction residual stress $\sigma_L$ of graphite substrate/CVD silicon carbide coated tube is 132.19 MPa. The type of obtained coating residual stress is tensile stress.

Embodiment 2: the residual stress test of the reactive sintering silicon carbide plate substrate/CVD silicon carbide coating.

Figure 7:
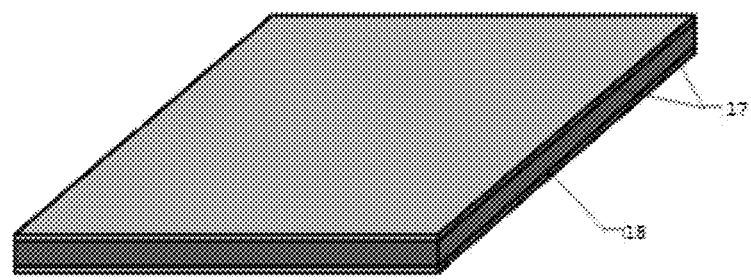
FIG. 7 shows a cross section schematic diagram of the graphite substrate/CVD silicon carbide coating plates in accordance with an embodiment of the present disclosure.
Figure 8:
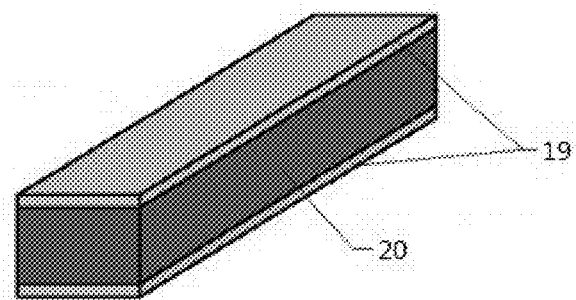
FIG. 8 shows a schematic diagram of the sample B in accordance with an embodiment of the present disclosure.

The schematic diagram of the cross section of the reactive sintering silicon carbide substrate/CVD silicon carbide coating plates is shown in FIG. 7, in which the label 17 is CVD silicon carbide coating, and the label 18 is reactive sintering silicon carbide substrate. The length of the plate L is 400 mm, the width B is 300 mm, the thickness H of the substrate is 20 mm, the upper coating thickness T1 is 200 μm, and the lower coating thickness T2 is 200 μm. Both sample A and sample B are bulk with the length of 50 mm; its cross section length is 4 mm, width is 3 mm, the area of the cross section is 12 mm$^2$. The schematic diagram of the taken sample B is shown in FIG. 8, and the label 19 in FIG. 8 is silicon carbide coating; label 20 is reactive sintering silicon carbide substrate. Both upper and lower coating thicknesses are 200 μm. Sample A adopts the same material as the measured reactive sintering silicon carbide substrate, and the sample B adopts the same preparation process as the to be measured reactive sintering silicon carbide substrate/CVD silicon carbide coating. The preparation temperature is 1100° C.

The width of the coating and the width of the substrate are the same, so the area ratio is equal to the thickness ratio. Once the thickness ratio of the substrate and the coating is determined, it can be substituted into the calculation.

The elastic modulus of the CVD silicon carbide coating and reactive sintering silicon carbide substrate are measured by the relative method. Specifically, the elastic modulus Ec of the silicon carbide coating is 440 GPa, and the elastic modulus Es of the substrate is 347 GPa.

Figures 1, 9:
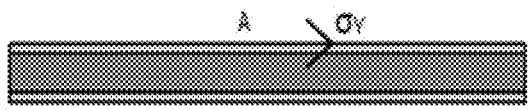
Figures 2, 9:
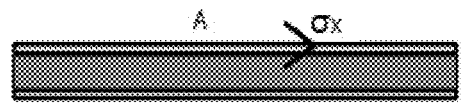
Figures 3, 9:
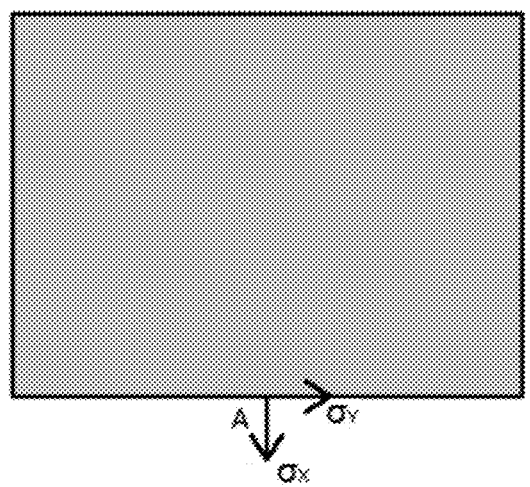

The residual stress of the to be measured reactive sintering silicon carbide substrate/CVD silicon carbide coating include the residual stress along X direction $\sigma_X$ and the residual stress along Y direction $\sigma_Y$. The front view, side view and top view of the force schematic view are shown in FIGS. 9-1 to 9-3 respectively.

The residual stress along X direction $\sigma_X$ of the to be measured reactive sintering silicon carbide substrate/CVD silicon carbide coating plates is tested as follows:

The cross-sectional area of the coating is $S_c=B\times(T_1+T_2)=120$ mm$^2$, and the cross-sectional area of the substrate is $S_s=B\times H=6\times10^3$ mm$^2$. The average thermal expansion coefficient of the coating and the substrate is obtained by testing sample A and sample B using the apparatus for testing residual stress in coatings. In particular, the thermal expansion coefficient $\alpha_c$ of the coating is $2.47\times10^{-6}/°$ C., the thermal expansion coefficient $\alpha_s$ of the substrate is $3.41\times10^{-6}/°$ C. The elastic modulus of the coating and the substrate, the cross-sectional area of the coating and the substrate and preparation temperature of the coating are input into the test apparatus, and the residual stress of the measured coating of the component can be obtained. Specifically, the residual stress $\sigma_X$ along X direction of the reactive sintering silicon carbide substrate/CVD silicon carbide coating plates is 403.37 MPa. Since the thermal expansion coefficient of the coating is less than that of the substrate, the type of obtained residual stress of the coating is compressive stress.

The Y direction residual stress $\sigma_Y$ of the to be measured reactive sintering silicon carbide substrate/CVD silicon carbide coating plates is measured as follows:

The cross-sectional area of the coating is $S'_c=L\times(T_1+T_2)=160$ mm$^2$, and the cross-sectional area of the substrate is $S'_s=L\times H=8\times10^3$ mm$^2$. The elastic modulus of the coating and the substrate, the cross-sectional area of the coating and the substrate and the preparation temperature of the coating are input into the test apparatus, and the residual stress of the measured coating of the component can be obtained. Specifically, the residual stress $\sigma_Y$ along Y direction of the reactive sintering silicon carbide substrate/CVD silicon carbide coating plates is 403.37 MPa. The type of obtained residual stress of coating is compressive stress.

The residual stress tests of two ceramic coating components demonstrate that the method of the present disclosure is not affected by the shape and size of the coating component. Based on the principle of the present disclosure, the method of the present disclosure is applicable to testing the residual stress caused by mismatch of thermal expansion coefficients of the coating and the substrate of any isothermal coating components, including metal coating and ceramic coating, etc.

The above description is only the specific implementation method of the present disclosure, but the protection scope of the present disclosure is not so limited. Those skilled in the art can easily think of change or replacement within the scope of technology disclosed by the present disclosure, which should be covered within the protection scope of the present disclosure. The protection scope of the present disclosure shall be determined by the terms of the claims.

What is claimed is:

1. A method for testing residual stress in coatings, comprising the following steps:
    obtaining elastic modulus of a coating and a substrate of a target object;
    obtaining a temperature during the coating preparation of the target object;
    obtaining a cross-sectional area of the coating and a cross-sectional area of the substrate of the target object;
    obtaining a thermal expansion coefficient of the coating $\alpha_c$ and a thermal expansion coefficient of the substrate $\alpha_s$ of the target object,
    wherein $\alpha_c$ and $\alpha_s$ are obtained through the following steps:
    preparing a sample A and a sample B, wherein the sample A is a sample of the substrate of the target object, and the sample B is a compound sample of which the substrate of the target object is compounded with the coating of the target object;
    obtaining the thermal expansion coefficients of the sample A and the sample B separately, wherein the thermal expansion coefficient of the sample A is $\alpha_s$; and
    obtaining the thermal expansion coefficient of the coating $\alpha_c$ of the target object through the thermal expansion coefficients of the sample A and the sample B; and
    calculating the coating residual stress $\sigma_c$ of the target object by the following formula:

$$\sigma_c = \left(\frac{S_s}{S_c}\right) \cdot \left[1 - \left(\frac{E_s S_s}{E_c S_c} + \frac{\alpha_c}{\alpha_s}\right) \bigg/ \left(1 + \frac{E_s S_s}{E_c S_c}\right)\right] \cdot E_s \alpha_s \Delta T_c,$$

wherein, $S_c$ is the cross-section area of the coating of the target object, $S_s$ is the cross-section area of the substrate of the target object, $E_c$ is the elastic modulus of the coating of the target object, $E_s$ is the elastic modulus of the substrate of the target object, and $\Delta T_c$ is the temperature during the coating preparation of the target object.

2. The method for testing residual stress in coatings according to claim 1, wherein an average thermal expansion coefficient of the coating of the target object from room temperature to the preparation temperature $\Delta T_c$ of the coating is determined as the thermal expansion coefficient of the coating $\alpha_c$, and an average thermal expansion coefficient of the substrate of the target object from room temperature to the preparation temperature $\Delta T_c$ of the coating is determined as the thermal expansion coefficient of the substrate $\alpha_s$, when the thermal expansion coefficient of the coating $\alpha_c$ and the thermal expansion coefficient of the substrate $\alpha_s$ of the target object are tested.

3. The method for testing residual stress in coatings according to claim 1, wherein the average thermal expansion coefficient of the coating and the average thermal expansion coefficient of the substrate of the target object are obtained by using a relative method.

4. The method for testing residual stress in coatings according to claim 1, wherein the substrates of the sample A and the sample B are prepared from the same material as the substrate of the target object, and the coating of the sample B is prepared from the same material and preparation process as the coating of the target object.

5. The method for testing residual stress in coatings according to claim 1, wherein the distribution of the coating of the sample B is symmetrical on the substrate of the sample B, so as to avoid bending deformation during temperature changing.

6. The method for testing residual stress in coatings according to claim 1, wherein sizes of both the sample A and the sample B adopt a sample size according to a test standard of thermal expansion coefficient.

7. The method for testing residual stress in coatings according to claim 1, wherein the elastic modulus of the coating and the substrate of the target object are obtained by using a relative method.

8. The method for testing residual stress in coatings according to claim 1, wherein the elastic modulus of the coating and the substrate of the target object are obtained by testing samples prepared from the same material as the target object.

9. The method for testing residual stress in coatings according to claim 1, wherein coating residual stress type of the target object is determined according to the thermal expansion coefficient of the coating and the thermal expansion coefficient of the substrate of the target object, wherein if the thermal expansion coefficient of the coating is larger than the thermal expansion coefficient of the substrate, the coating residual stress is tensile stress, and otherwise, the coating residual stress is compressive stress.

10. An apparatus for testing residual stress in coatings, comprising:
    a heating furnace, for heating a sample in order to make the sample expand with heat;
    a temperature control device, for controlling heating temperature of the heating furnace;
    a slide rail mechanism, for being connected with the heating furnace, the heating furnace sliding along a track of the slide rail mechanism;
    a quartz bracket, provided with a sample holder;
    a drive rod, for transferring expansion displacement of the sample;
    a micro displacement measurement device, for testing the expansion displacement of the sample transferred by the drive rod; and
    a computer, for receiving relevant data and organizing the relevant data into parameters for calculating the coating residual stress, and obtaining the coating residual stress $\sigma_c$ of the target object through processing the parameters according to the following formula:

$$\sigma_c = \left(\frac{S_s}{S_c}\right) \cdot \left\{1 - \left[\frac{E_s S_s}{E_c S_c} + \frac{\alpha_c}{\alpha_s}\right] \bigg/ \left[1 + \frac{E_s S_s}{E_c S_c}\right]\right\} \cdot E_s \cdot \alpha_s \cdot \Delta T_c$$

wherein, $S_c$ is the cross-section area of the coating of the target object, $S_s$ is the cross-section area of the substrate of the target object, $E_c$ is the elastic modulus of the coating of the target object, $E_s$ is the elastic modulus of the substrate of the target object, $\alpha_c$ is the thermal expansion coefficient of the coating of the target object, $\alpha_s$ is the thermal expansion coefficient of the substrate of the target object, and $\Delta T_c$ is the temperature during the coating preparation of the target object.

11. The apparatus for testing residual stress in coatings according to claim 10, wherein the quartz bracket comprises a first quartz bracket and a second quartz bracket, which are internally provided with the sample holder separately for holding a sample; and
    the drive rod comprises a first drive rod and a second drive rod, which are used for transferring the expansion displacement of the samples in the first quartz bracket and the second quartz bracket separately.

12. The apparatus for testing residual stress in coatings according to claim 10, wherein test resolution of the micro displacement measurement device is smaller than 0.2 mm.

* * * * *